United States Patent [19]
Leonard et al.

[11] Patent Number: 6,063,044
[45] Date of Patent: May 16, 2000

[54] APPARATUS FOR MEASURING MUSCLE TONE

[76] Inventors: Charles T. Leonard, 5000 Pattee Canyon, Missoula, Mont. 59803; Eugene L. Mikhailenok, Prospect Morisa Toreza 7 1/3-28, St. Petersburg, U.S.S.R., 194214

[21] Appl. No.: 09/295,277

[22] Filed: Apr. 20, 1999

[51] Int. Cl.$^7$ .............................. A61B 5/103; A61B 5/117
[52] U.S. Cl. ............................................................. 600/587
[58] Field of Search ............................... 600/587; 128/55

[56] References Cited

U.S. PATENT DOCUMENTS

| | | | |
|---|---|---|---|
| 3,133,355 | 5/1964 | Gordon | 33/172 |
| 4,159,640 | 7/1979 | Leveque et al. | 73/81 |
| 5,224,469 | 7/1993 | Mocny | 128/55 |
| 5,879,312 | 4/1999 | Imoto | 600/587 |

OTHER PUBLICATIONS

Waldorf, T., et. al., The Comparative Assessment of Paraspinal Tissue Compliance in Asymptomatic Female and Mail Subjects in Both Prone and Standing Positions, *J. of Manipulative and Physiological Therapeutics*, vol. 14, No. 8, p. 457–461, Oct. 1991.

Fischer, A.A., Documentation of Myofascial Trigger Points, *Arch Phys. Med. Rehabil.*, vol. 69, p. 286–291, Apr. 1988.

Gevlich, G.I., et. al., Evaluation of Skeletal Muscle Tone by Recording Lateral Rigidity, *Kosmicheskaya Biologiya I Aviakosmicheskaya Meditsina*, vol. 17, No. 5, p. 86–89, Sep.–Oct. 1983.

Fischer, A.A., Tissue Compliance Meter for Objective, Quantitative Documentation of Soft Tissue Consistency and Pathology, *Arch. Phys. Med. Rehabil.*, vol. 68, p. 122–125, Feb. 1987.

Fischer, A.A., et. al., Muscle Tone in Normal Persons Measured by Tissue Compliance, *J. of Neurological & Orthopaedic Medicine & Surgery*, vol. 8, No. 3, p. 227–233, Oct. 1987.

Horikawa, M., et. al., Non–invasive Measurement Method for Hardness in Muscular Tissues, *Medical & Biological Engineering & Computing*, vol. 31, p. 623–627, Nov. 1993.

Latimer, J., et. al., Evaluation of a New Device for Measuring Responses to Posteroanterior Forces in a Patient Population, Part I: Reliability Testing, *Physical Therapy*, vol. 76, No. 2, p. 158–165, Feb. 1996.

Vain, A., et. al., Grading Rigor Mortis with Myotonometry—A new Possibility to Estimate Time of Death, *Forensic Science International*, vol. 56, p. 147–150, 1992.

*Primary Examiner*—Max Hindenburg
*Assistant Examiner*—Brian Szmal
*Attorney, Agent, or Firm*—Frank G. Morkunas

[57] ABSTRACT

An apparatus for measuring muscle condition comprising an upper housing having a top; a lower housing having a base at one end and a top member at another end and a guide member adjacent to the top member; a probe member connected to the upper housing and having an end cap which, when the apparatus is at rest, is adjacent to the base to thereby define a plane, and a bias member attached to the end cap at one end and attached to the top member of the lower housing at another end, the probe member being slidably attached to the lower housing; a force measuring sensor for measuring the amount of force being exerted when the top of the apparatus is pressed; a shift measuring sensor for measuring the distance the probe member moves beyond the base; and a controller to direct the number of single measurements of force and of shift to be taken during a single measurement cycle, to control the amount of force to be exerted at each single measurement, to record measurement data collected, to derive a measurement average for a session constituting more than one measurement cycle, and to display and compare measurement averages between sessions.

10 Claims, 5 Drawing Sheets

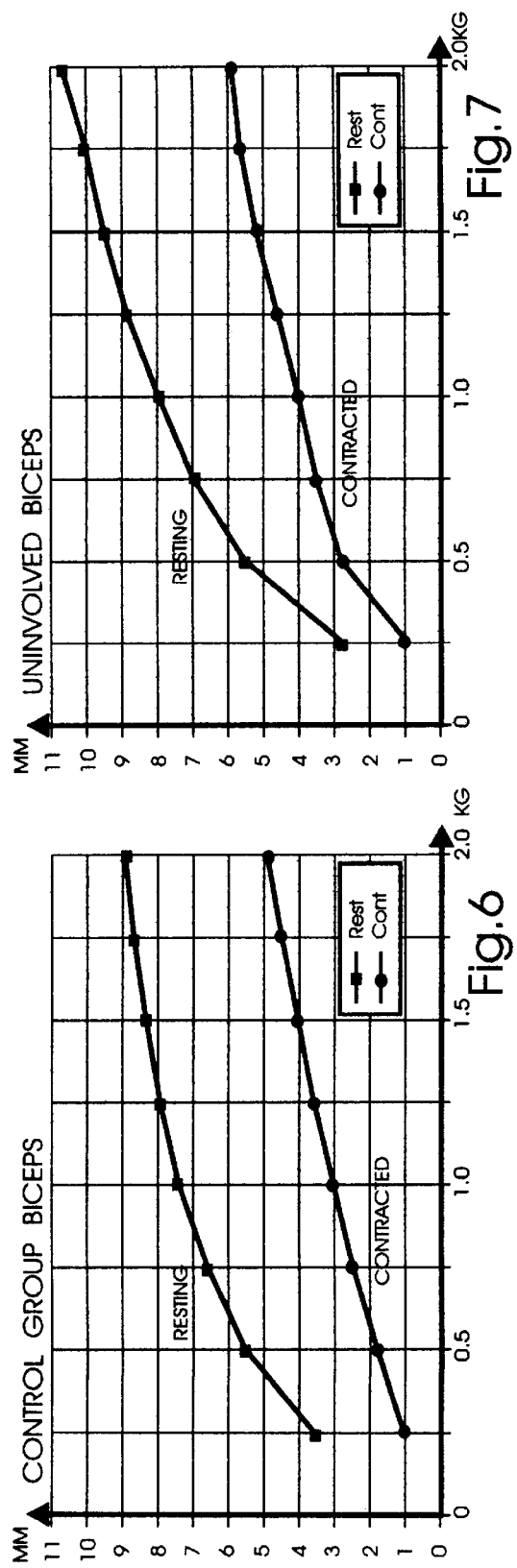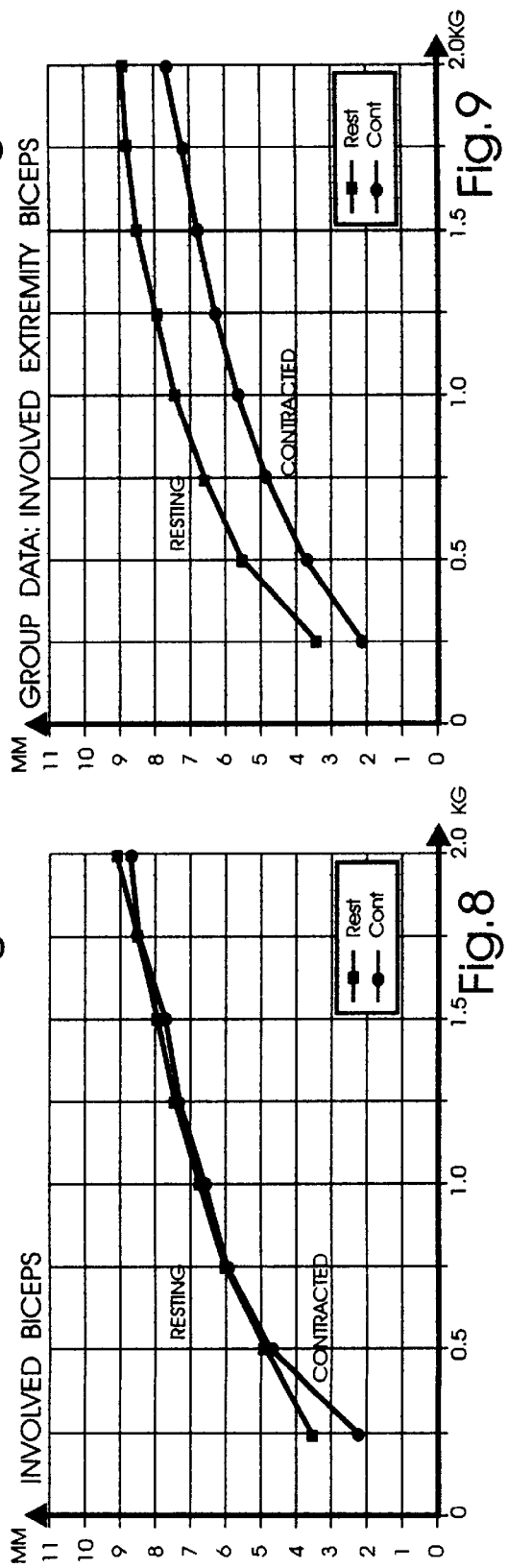

APPARATUS FOR MEASURING MUSCLE TONE

CROSS REFERENCES TO RELATED APPLICATIONS

Not applicable.

STATEMENT REGARDING FEDERALLY-SPONSORED RESEARCH OR DEVELOPMENT

Not applicable.

BACKGROUND OF THE INVENTION

This present invention relates to an improvement in medical and scientific devices for measuring physical attributes of muscles, and more particularly to measuring muscle tone, compliance, and paresis. The is accomplished by incorporating a translating probe or prod which is in communication with one or more transducers which act to quantify the force applied to skin and underlying tissues (e.g., muscle) and the amount of tissue displaced thereby. Results are stored, analyzed, and compared against previous results via a computer interface.

Health-care personnel, generally within the specialties of neurology, neurosurgery, rehabilitation, and physical medicine, evaluate and treat patients who have had or currently have various disabilities as a result of injury or disease to muscle or the nervous system, or a combination of both thereto. A common sequelae to many neurological conditions are pathological changes in muscle tone, compliance, and strength—all of which contribute to a disorder known as the spastic condition. Generally speaking, muscle tone may be described as the background tension within a muscle at rest. Clinically, muscle tone is typically tested by passively moving a patient's limb into flexion and extension and subjectively monitoring the amount of resistance offered by the muscle during the movement. Attempts have been made to lessen the subjectivity of this form of testing. The Ashworth scale is one such attempt. In this regard, an ordinal scale ranging from 1–4 is used to assess muscle tone. The scale is the clinical gold standard used for muscle tone assessments but it remains a less than optimal test because of poor test-retest reliability, poor inter-tester reliability, and a clustering effect (i.e., most patients receive a similar rating regardless of level of severity of disability).

Muscle compliance basically is the amount of force produced by a muscle in response to lengthening of that muscle; it is the inverse of elasticity—the intrinsic quality of a muscle that resists stretch. Muscle compliance testing is typically done with complex, specialized, and expensive laboratory equipment. As such, it is not a widely used clinical testing procedure.

Muscle strength is the amount of force that can be generated by a muscle. The amount of weight an individual can lift has always been equated with muscle strength. Pain or patient intervention, however, can interfere with an accurate assessment of an individual's muscle strength. Increasingly, muscle strength is being tested with various computerized machinery or with surface electromyography. Paresis is associated with muscle strength in that it is the weakness manifested by an individual during muscle contraction.

Spasticity in an individual is a complex combination of overall muscle condition and, therefore, is a difficult condition to define with a great detail of specificity. Basically, spasticity encompasses combined changes in muscle tone, muscle compliance, and muscle strength. A person suffering from spasticity generally experiences an increase in muscle tone and muscle compliance while exhibiting a decrease in muscle strength.

A reliable, valid, fast, easy, and relatively inexpensive means to quantify and analyze each of the conditions described above has proved to be rather elusive.

There are also numerous protocols currently in use that are employed to decrease spasticity and alter muscle tone. Quantifying the effectiveness of these protocols, however, has also been difficult because of the lack of an appropriate test instrument which can quantify pre- and post-treatment outcomes.

Our present invention is a reliable device which is capable of quickly and effectively measuring and quantifying muscle tone, muscle compliance, and muscle strength. The present invention is a hand-held electronic device that can be interfaced with a computer so that measurements may be stored and analyzed with, and against, other measurements previously taken and recorded. It is a non-invasive, painless, easy-to-use device which provides accurate, reliable, and reproducible results. In operation, the device is placed on a patient's skin. A probe is gently pressed downward on the skin surface. The probe does not penetrate the skin but merely pushes against the skin. The measurements taken by the present invention includes the amount of deformation (skin displacement) which results when a given unit of force is exerted on the underlying muscle, first, in its relaxed (resting) state and, second, in its maximally contracted state. Values derived from a rested state provide an accurate assessment of muscle tone and muscle compliance. Values derived from a contracted state provide an accurate assessment of muscle strength. The differences between the two sets of values when graphed linearly reflect slopes whose differences represent an assessment of the severity level of the person's spasticity.

Quantifying the spastic condition would have a considerable economic impact for the health-care industry. For instance, cerebral vascular accidents (CVAs—commonly referred to as 'stroke') affect over 500,000 Americans annually. Approximately one-third are permanently disabled. Rehabilitation costs for those disabled exceeds $25 billion annually. Spasticity and muscle tone alteration almost always follow a stroke. To date, there are numerous treatments for the condition. Such treatments include various pharmacological agents, surgeries such as dorsal root rhizotomies (surgical procedure to reduce muscle tone and, thereby, spasticity), casting the spastic limb, and various physical therapies. Because there is no easy and reliable method to quantify spasticity, treatment protocols tend to rely on trial an error rather than any proven effectiveness.

The ability to quantify one's spastic condition will take on increased significance as different drugs are developed to mimic specific neurotransmitters within specific neural pathways. Attempts are underway to identify the dysfunctional neural pathways associated with stroke and other neurological diseases. dorsal root rhizotomy is gaining in popularity although the longterm effect is uncertain and may not be a real cure. Currently there is no accurate and reliable manner or instrument to properly assess spasticity. In today's world of managed health care, the emphasis is clearly on effective treatment. The present invention paves the way for effective treatment regimens.

Devices based on the concept of comparing force and displacement measurements exist but they tend to be large, cumbersome devices, and lacking in requisite accuracy. One such similar device can be found in U.S. Pat. No. 3,133,355 issued to Gordon on May 19, 1964. It, however, relates only to measuring muscle tone (resting muscle tension). Although suited for the intended purpose, it is a rather intrusive device, cumbersome to operate in that it requires precise positioning, and is not capable of measuring muscle compliance, measuring muscle strength, or recording and analyzing such data as collected. Other instruments include that addressed by Fischer's tissue compliance meter. This instrument uses a force gauge which is pressed into the muscle at a known force and measures the depth of penetration with a spring gauge. It requires 2–3 kg (kilograms) or more of force and is used to measure depths at 1 kg-force increments from 1–5 kg. All these prior art instruments lack precision and lack the functional ability to measure all three conditions, to record the results, and to analyze the results against previous results. In short, a need existed for a device and method which could quantify muscle tone and would permit for repeated measurements with precision and further permit comparisons of such measurements over time. The present invention employs highly accurate transducers aligned for accuracy and to prevent time-lag between transducer recordings. Prior art devices use spring gauges which are inherently inaccurate and show fatigue and increased inaccuracy over time.

The present invention represents a unique combination of newly developed structure and process which, together provide for accurate and reliable assessments of spasticity, muscle tone, muscle compliance, and muscle strength. Analysis of the measurements may be performed by any conventional computer, attachable to the device, which record the results and, through any conventional output device (monitor, printer), provides the results to a healthcare practitioner immediately.

Accordingly, several objects and advantages of the present invention are to:

a. provide for an economical, yet accurate apparatus for measuring muscle conditions;

b. provide for an apparatus which is capable of measuring force and depth relative to that force when applied to a muscle;

c. provide for an apparatus which is simple to use; and d. provide for an apparatus that is capable of multiple measurements of force/depth, recording such measurement, and storing such measurements for future use and comparison relative to therapy and treatment effectiveness.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF SUMMARY OF THE INVENTION

The above-noted problems, among others, are overcome by the present invention. Briefly stated, the present invention contemplates an apparatus for measuring muscle condition comprising an upper housing having a top; a lower housing having a base at one end and a top member at another end and a guide member adjacent to the top member; an inner housing probe member connected to the upper housing and having an end cap which, when the apparatus is at rest, is adjacent to the base to thereby define a plane, and a bias member attached to the end cap at one end and attached to the top member of the lower housing at another end, the probe member being slidably attached to the lower housing; a force measuring sensor for measuring the amount of force being exerted when the top of the apparatus is pressed; a shift measuring sensor for measuring the distance the probe member moves beyond the base; and a controller to direct the number of single measurements of force and of shift to be taken during a single measurement cycle, to control the amount of force to be exerted at each single measurement, to record measurement data collected, to derive an measurement average for a session constituting more than one measurement cycle, and to compare measurement averages between sessions.

The foregoing has outlined the more pertinent and important features of the present invention in order that the detailed description of the invention that follows may be better understood so the present contributions to the art may be more fully appreciated. Additional features of the present invention will be described hereinafter which form the subject of the claims. It should be appreciated by those skilled in the art that the conception and the disclosed specific embodiment may be readily utilized as a basis for modifying or designing other structures and methods for carrying out the same purposes of the present invention. It also should be realized by those skilled in the art that such equivalent constructions and methods do not depart from the spirit and scope of the inventions as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIGS. 6–9 are graphs representative of readings from several sessions.

DETAILED DESCRIPTION OF THE INVENTION

Figure 5:
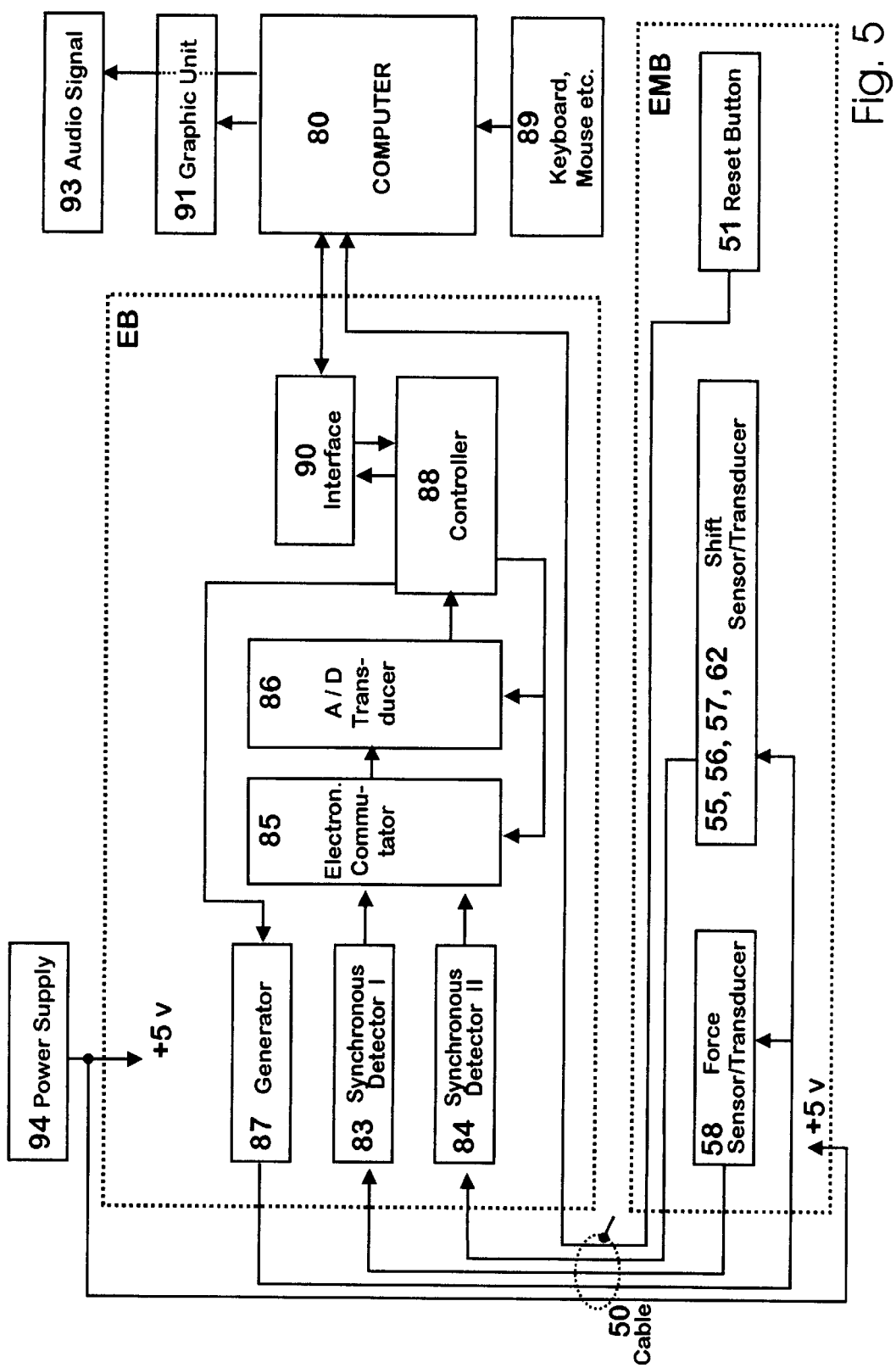
FIG. 5 is a block diagram illustrating the conventional components of the apparatus.

The present invention is directed to a novel apparatus and method for determining muscle tone, muscle compliance, and muscle strength—and overall for determining the degree or severity of spasticity—by obtaining precise multifarious data which can be quantified, stored, analyzed, and compared over time. FIGS. 1–4 illustrate the apparatus in detail. FIG. 5 represents the major components associated with the apparatus. The apparatus makes measurements while the muscle tissue involved is being mechanically displaced by a probe descending onto the skin. Both the force involved and the depth (displacement) of the probe that is displacing the muscle tissue are recorded. Multiple increments of force and depth readings (each single reading of force/depth is referred to as a measurement) are recorded during a single act of displacement (multiple measurements is referred to as a cycle; numerous cycles encompass a session). In this regard, where F is a maximal applied force during one act of muscle displacement and dF is change in force being applied to the muscle tissue, we have the following: n=F/dF. The muscle tissue to be measured is automatically incrementally increased by the apparatus to gradually, smoothly, and progressively displace the muscle tissue by a movable probe as pressure is exerted from the top of the apparatus and onto the muscle tissue.

After the completion of a cycle, the apparatus is removed from contact with the skin and readied for the next cycle. Therefore, during a single cycle, numerous displacement depths are measured simultaneously along with the force required to achieve that depth. A cycle should be repeated multiple times in the same area, graphed, and averaged in order to establish precision of measurement. Generally between 5–8 cycles are sufficient to establish an accurate measure. Also, generally, the first session should be performed on a muscle in its relaxed state followed by a session of that same muscle in its contracted state. These two sessions provide information necessary to assess the overall condition of the muscle involved from which future sessions will be compared to establish progress or regression and, depending on the results, alter the treatment or therapy. The averages from each session are graphed. The greater the differential between the two scopes of the graphic displays, the better the condition of the muscle. FIGS. 6–9 illustrate graphs generated from several different testing sessions involving various test subjects.

Figures 1, 2:
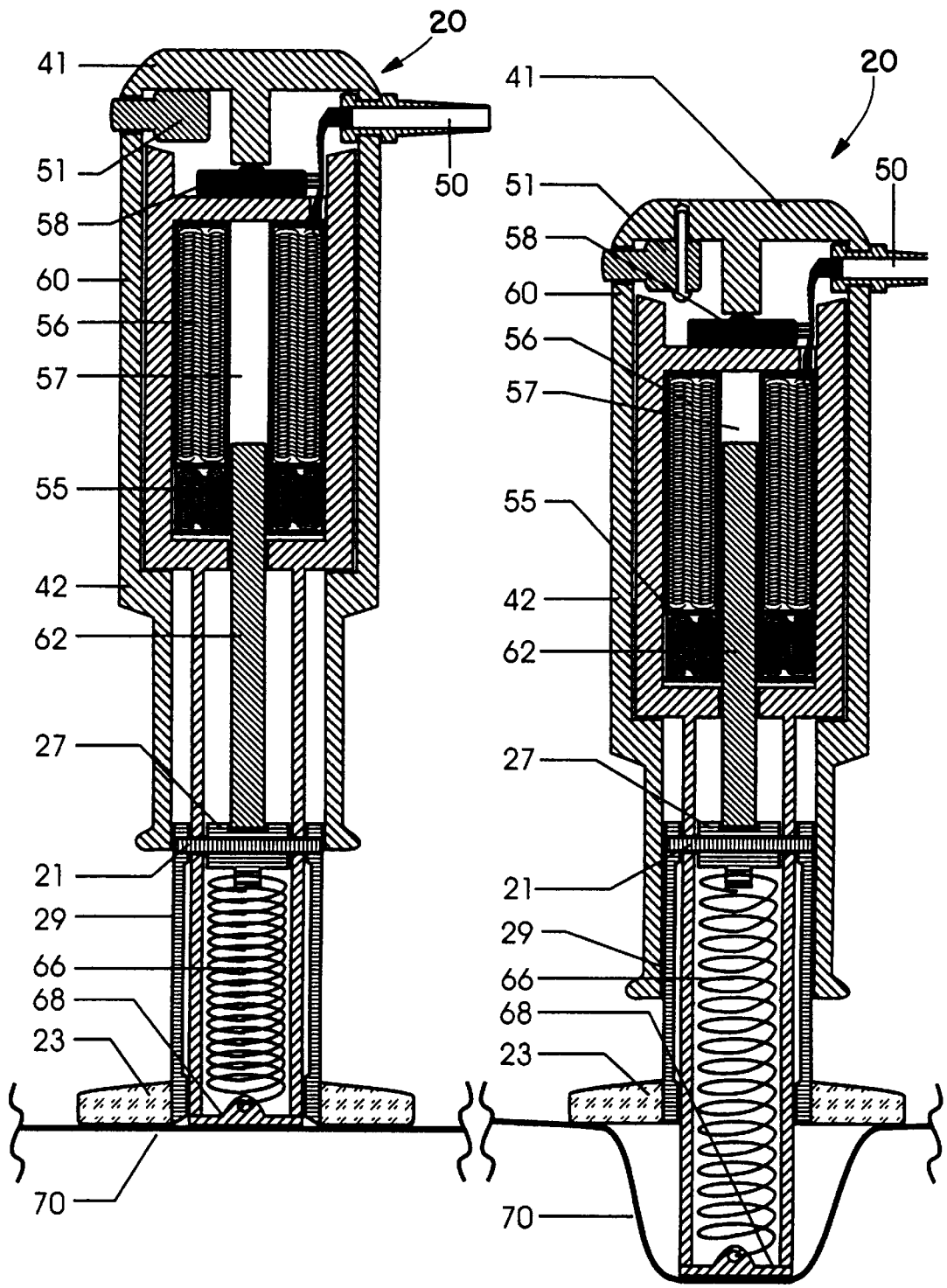
FIG. 1 is a cross-section view of the apparatus in a resting state.
FIG. 2 is a cross-section view of the apparatus in an operational state.
Figures 3, 4:
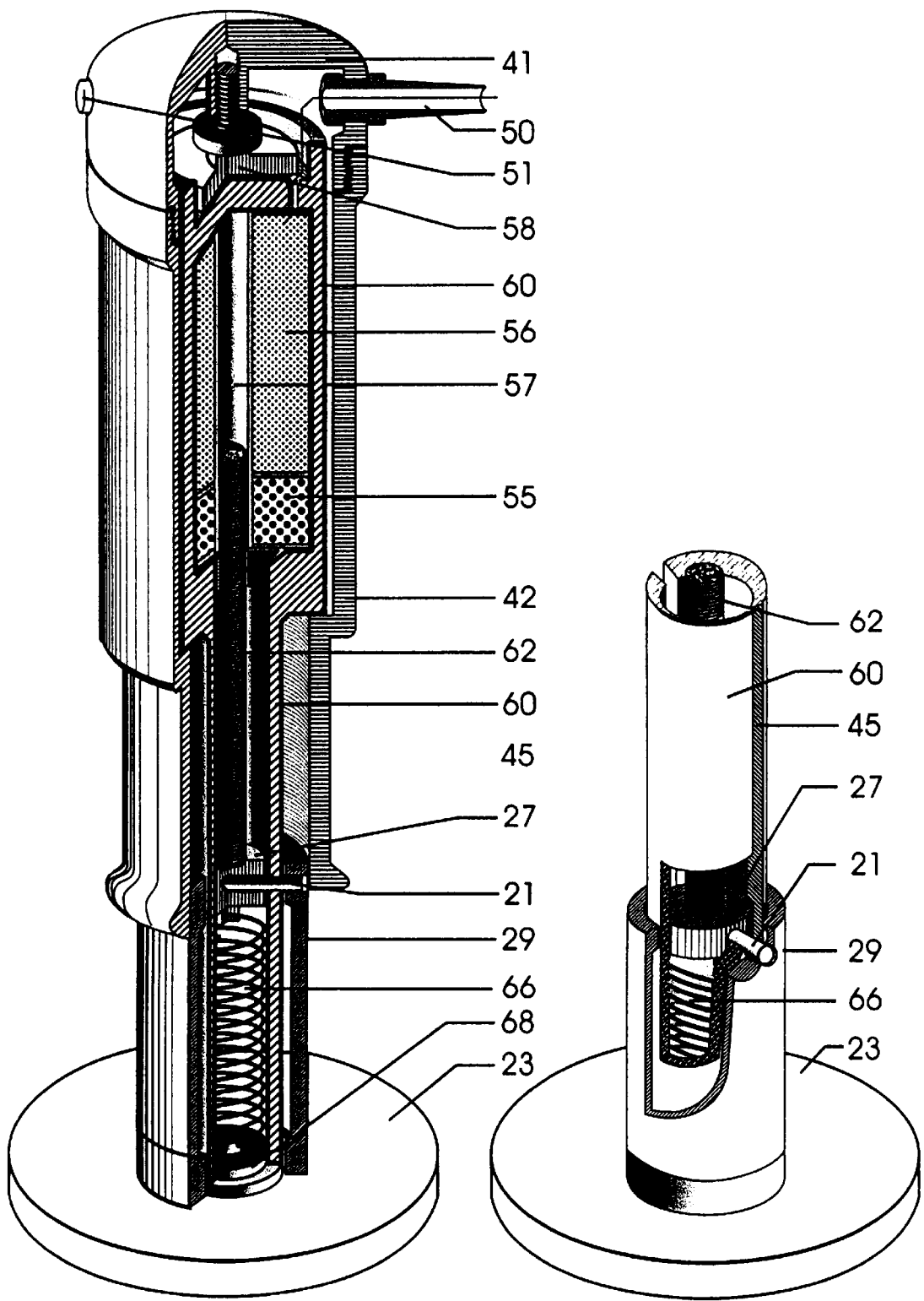
FIG. 3 is a perspective cut-away view of the apparatus.
FIG. 4 is a perspective partial view of the lower housing and a portion of the inner housing of the apparatus.

Referring now to the drawings in detail and in particular to FIG. 1, reference character 20 generally designates an apparatus for simultaneously measuring muscle tone, muscle compliance, and muscle strength constructed in accordance with a preferred embodiment of the present invention. For clarity of understanding, reference also should be made to FIGS. 1–4. The apparatus 20 is basically comprised of an upper housing member 42, a lower housing member 29, an internal housing member 60, a conventional strain gauge or force measuring transducer/sensor 58, and a conventional distance-measuring gauge or shift transducer/sensor (represented here as a transformer with windings 55 and 56 which translate over a core or ferro-magnetic bar 62 with a space 57 defined within the transducer).

The inner housing member 60 is contained within the upper housing member 42. A strain gauge or force transducer/sensor 58 is adjacent to and in direct contact with the top of the upper housing member 42 and secured to the inner housing member 60. The windings 55, 56 of the shift transducer and the space 57 defined thereby are contained within the inner housing member 60. Therefore, as the upper housing member 42 is being depressed, generally by exerting pressure on the top of the upper housing member 42, this causes the inner housing member 60 to slide downward below the bottom plane of the apparatus 20 and press the end cap 68 of the inner housing member 60 into the skin 70. The inner housing member 60 has at least two vertically disposed, opposing guides or slots 45 extending upward and downward from approximately its mid-section. Pins or fasteners 21 from the bottom housing member 29 project through the slots 45 and, in combination (slots 45 and pin 21) function to movably retain the inner housing member 60 to the lower housing member 29 and to guide the inner housing member 60 as it slides up and down within and beyond the lower housing member 29.

The lower housing member 29 extends downward from the bottom portion of the upper housing member 42 and has a base 23 at the bottom of the lower housing member 29 which is generally wider than the width of the inner housing member 60. The pin or fastener 21 traverses the lower housing member 29 and its top 27 (and through the slots 45 as described above) thereby securing these elements in place. The slots 45 are generally perpendicular to the plane of the base. The bottom of the ferro-magnetic bar 62 is secured to the top 27 of the lower housing member 29.

A spring-like member 66 is connected to the bottom of the inner housing member 60 adjacent to the end cap 68. This spring-like member 66 also is connected at the other end to the top 27 of the lower housing member 29. The spring-like member 66 causes the inner housing member 60 to return to its resting position (non-extended) after the apparatus 20 is removed from the skin 70.

FIG. 5 represents the electrical components of the apparatus. For ease of explanation, it has been broken down into two parts; (1) an electro-mechanical block (EMB) comprising the force transducer 58 and the shift transducer 55, 56, 57, 62 contained within the apparatus 20, and (2) an electronic block (EB) 83–90 comprising the electronic components to which the device is attachable. The EB may be, but need not be, an external set of components connectable to the apparatus 20 via the electrical connector or cable 50.

The EB comprises two or more sets of synchronous detectors 83,84 (one for the force tranducer and one for the shift transducer). These are conventional components readily available in the open market. One such component suitable for use in the apparatus as the synchronous detector includes, but is not limited to an amplifier, Model LM-701 as manufactured by Texas Instruments Corporation, or equivalent suited for the intended purpose. A component suitable for use in the apparatus as the force transducer includes, but is not limited to, Model BLC-500 as manufactured by Logitech, Inc., or equivalent suited for the intended purpose. Another component suitable for use in the apparatus as the shift transducer includes, but is not limited to, Model 400 series manufactured by B1 Technologies Corporation, or equivalent suited for the intended purpose. Each of the synchronous detectors 83, 84 are connected to a conventional electronic commutator 85 and controlled by a conventional programmable controller 88 having, among other features, programming, processing, storage, and memory capabilities. A conventional analog-digital transmitter 86 links the electronic commutator 85 to the controller 88. Components suitable for use with the apparatus include, but are not limited to, Model PIC1400/04 as manufactured by Microchip (for the programmable controller 88) or equivalent suited for the intended purpose; Model Max 398, as manufactured by Maxim (for the electronic commutator 85) or equivalent suited for the intended purpose; and Model Max 199 as manufactured by Maxim (for the analog-digital transducer/converter 86) or equivalent suited for the intended purpose.

The controller 88 is linked to a conventional computer 80 through a conventional interface 90. Also connectable to the computer is an output device which may be, but is not limited to, a monitor or a printer for displaying and or memorializing measurements taken and graphing changes thereto over the course of time. The EMB of the apparatus 20 and the controller 88 are powered by any suitable conventional 5-volt power source 94. The computer is powered by any conventional power source (not shown).

In operation the apparatus 20 is first turned on. It may have its own internal power source or rely on an externally connected power source (not shown). A signal (audible or visual) is emitted indicating the apparatus 20 is in the ready-mode for operation. The base 23 is applied to the skin surface 70 of the muscle portion to be tested. See FIG. 1. As illustrated here, the base 23, the end cap 68, and the skin 70 generally are in linear alignment. The user exerts downward pressure from the top 41 of the apparatus 20. The base 23 does not move with this downward force but remains in place on the surface of the skin 70, maintaining linear alignment therewith, while the inner housing member 60 (which is connected to the upper housing member 42) is pushed downward into the skin 70 thereby pressing muscle tissue in the process. Refer to FIG. 2. The pressure is automatically incrementally increased at increments of 250 g (grams) from 0 to a maximum of up to 5 kg (kilograms) and force-to-depth measurements are taken. We have found that the maximum of 2 kg is sufficient providing for 8 measurements to the cycle. It must be understood that the apparatus may be programmed to measure displacement at any force amount—250 g being best suited for establishing one's muscle condition with greater accuracy. A signal 93 (either audible or visual) is emitted once the maximum force of 2 kg is attained and the apparatus automatically resets for the next cycle.

For proper placement of the apparatus 20 on the specific area to be tested, it is best that the base 23 be constructed of a relatively transparent or transparent-like material. The amount of pressure being exerted incrementally by a user on the apparatus 20 is being measured by the force transducer 58 with each preset increment (increments of 250 g up to 2 kg). Measurement data is collected and transmitted via the electronic connector 50 of the apparatus 20 to the EB as described above.

As the inner housing member 60 is moving downward into the skin 70 it, through the shift transducer it houses, is taking simultaneous depth readings at each force increment of, in this example, 250 g. Recall, the lower housing member 29, being connected to the base 23 remains stationary. The ferro-magnetic bar 62, connected to the lower housing member 29 also remains stationary. As the inner housing member 60 moves downward, with its electro-magnets 55, 56 and the space 57 defined therein, they ride downward around the ferro-magnetic bar 62 thereby generating an electric signal that is representative of the inner housing member's 60 extent of muscle tissue displacement. For best and the most accurate results, the end cap 68 should be configured of any atraumatic shape; circularly-shaped is preferred.

After all the measurements, pressure and displacement for each increment of force, are taken, a concluding signals alerts the operator that the cycle has been completed and prevents the apparatus 20 from taking further measurements for that cycle. The number of measurements constituting a cycle can vary with the user and the intent of the examination. The apparatus 20 is capable of performing a single measurement of force/displacement or multiple incremental measurements of force/displacement at any programmed increment of force desired.

Multiple measurements per cycle are preferred and several cycles should be performed. Five to eight such cycles are preferred and suited for accuracy. We have found that depth measurements should be recorded at each force increment of 250 g until the total force exerted attains 2 kg thereby providing eight such force/depth measurements per cycle. The readings from each cycle are averaged and stored in memory. After the concluding signal is detected by the user, the user removes the apparatus 20 from the skin surface. The spring-like member 66 causes the inner housing member 60 to retract back together with the upper housing member 42 of the apparatus 20. The tension of the spring-like member 66 is not so strong as to affect the measurements being taken yet strong enough to retract the inner housing member 60 after the apparatus 20 is removed from the skin.

As every single measurement is taken by the force transducer 58 and the shift transducer 55, 56, 57, 62 the electric signals representing the respective measurements of force (pressure applied at the top of the apparatus) and shift in distance (depth of the inner housing member 60 into the skin) are transmitted through the electrical connector 50 to the EB and into the inlets of the respective synchronous detectors 83, 84. Here the variable voltages from the respective pressure/shift transducers are rectified, filtered, and passed first to the commutator 85 and then to the analog-digital transducer 86. This analog-digital transducer 86 produces a signal in binary code which is proportional to the respective force and shift values received from the respective measuring gauges (i.e., force transducer and shift transducer). The activity is controlled by the programmable controller 88 which, after receiving a command from a user via the keyboard or other suitable input device 89, then directs the generator 87 to initiate a measurement process. A typical generator suitable for use is Model SG-615 as manufactured by Epson Electronics of America, Inc., or equivalent suited for the intended purpose.

The result of this circuitry allows measurements of force and depth (displacement or distance) to be made on a muscle being displaced by the inner housing member 60 while the force applied is incrementally increasing. This results in continuous depth-load data and a tonometric plot is generated and displayed or printed. The magnitude and shape of the plot is influenced both by mechanical factors of muscle tissue (its hardness under lateral deformation and its compliance) and by reflex responses to muscle stretch that occurs during the process. Thus, the tonometric plot pattern characterizes two of the primary determinants of muscle (i.e., muscle compliance and stretch reflexes).

Figure 10:
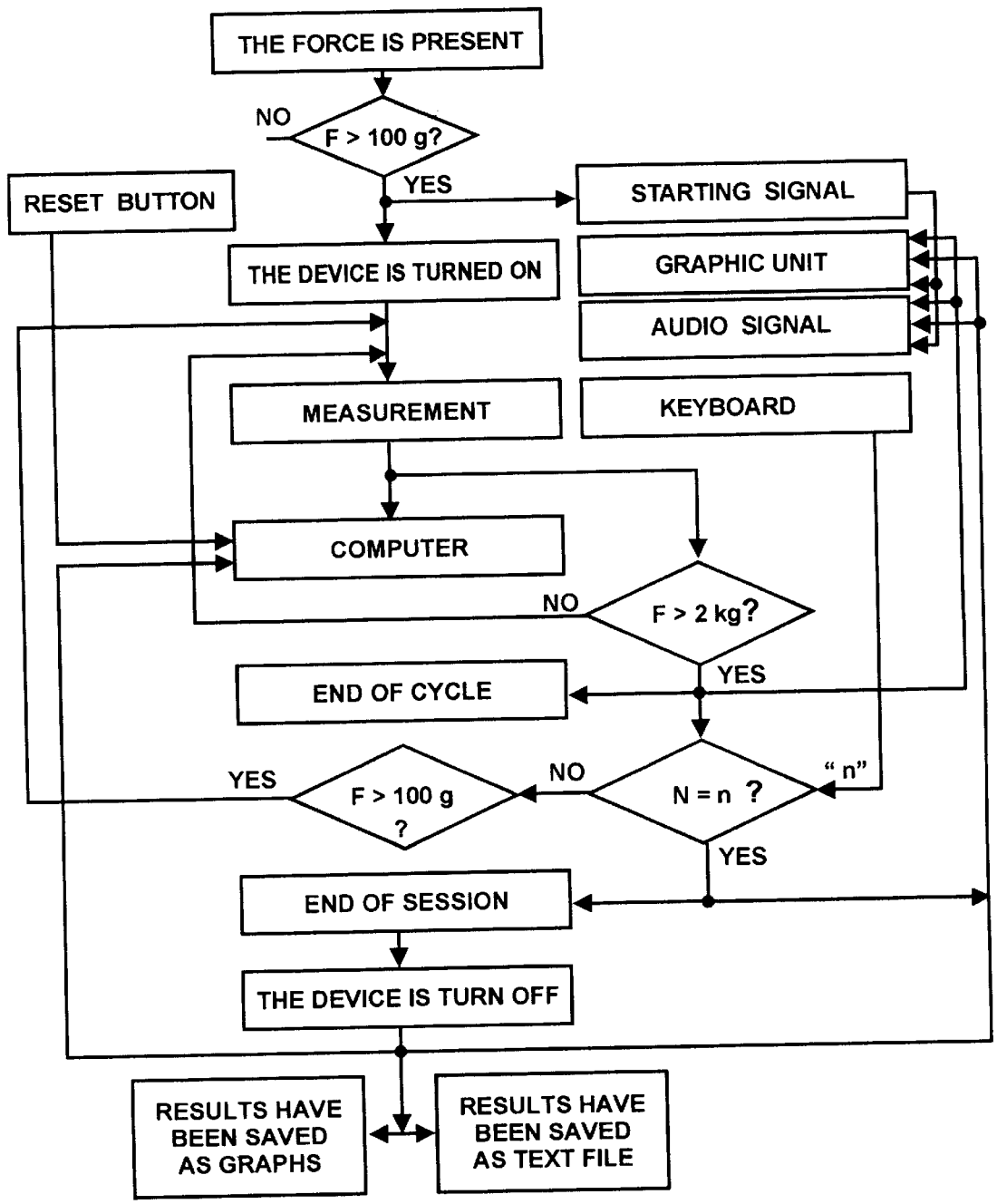
FIG. 10 is a flow chart on the operation of the apparatus.

FIG. 10 represents a flow chart depicting the overall operation of the apparatus. Generally the starting signal for measurement generally is the presence of a 100 g force on the apparatus 20 as detected by the force transducer 58; but this can be regulated or programmed differently. As described above for our preferred example, when a force of 250 g is achieved, the shift value (as defined by the new position of the ferro-magnetic bar 62 within the space 57 in relation to its previous position therein) will be detected by the shift transducer and the results transmitted to the EB. All values received will be stored in the memory of the computer 80. The process is repeated at each increment of 250 g increase in force applied up to a maximum of 2 kg. When the 2 kg level is attained, a signal is generated altering the user of such thereby closing that measurement cycle. At this point the programmable controller 88 automatically resets and will not detect any further signals from the EMB until the pressure reading attains its starting value. The shift values for each 250 g increment of force can be displayed on the output device 91, be it a monitor or a printer, in graph or numeral form. All measurement cycles and sessions may be stored, analyzed, and compared against prior measurement cycles and session and future measurement cycles and sessions.

In any one measurement cycle is detected by the operator to be inaccurate because, for example, it was not performed correctly, excessive movement or jarring occurred during the process, or the like, the apparatus 20 is equipped with a reset member 51 which, if executed, will void that last measurement cycle and recording thereof, while leaving all previous measurement cycles in that session undisturbed. The reset member is a conventional reset member. One such component suitable for use in the apparatus as the reset member includes, but is not limited to, Model CH-172-ND manufactured by Digikey Company, or equivalent suited for the intended purpose.

The versatility of the present invention also lies in the fact that a user, utilizing the input device 89, may request through the computer 80 any one or more types of measurements to be made for any one or more measurement cycles or sessions, to store data received from the measurements, cycles, and sessions and to compare previously stored data against newly received data as progressively received thereby permitting the user to quickly and easily discern the progression or regression of a person's condition and thereby direct or redirect treatment and therapy accordingly.

As described above, the present invention is capable of multiple measurements of a single area for muscle tone, muscle compliance, and muscle strength. As such, it is further capable of distinguishing between varying degrees of severity of spastic involvement and is capable of determining relative levels that abnormal muscle tone or paresis contributes to one's particular disability.

The present disclosure includes that contained in the present claims as well as that of the foregoing description. Although this invention has been described in its preferred forms with a certain degree of particularity, it is understood that the present disclosure of the preferred form has been made only by way of example and numerous changes in the details of construction and combination and arrangement of parts and method steps may be resorted to without departing from the spirit and scope of the invention. Accordingly, the scope of the invention should be determined not by the embodiment[s] illustrated, but by the appended claims and their legal equivalents.

The invention claimed is:

1. An apparatus for measuring muscle condition comprising:
   a. an upper housing having a top;
   b. a lower housing having a base at one end, a top member at another end, and a guide member connecting said lower housing to said top member;
   c. a movable inner housing having a probe member connected to its bottom, said inner housing connected to said upper housing, said probe member having an end cap which, when the apparatus is at rest, is adjacent to said base thereby defining a plane, and further having a bias member having a first end and a second end wherein said first end is attached to said end cap and said second end is attached to said top member of said lower housing, said probe member further having means for slidably attaching to said lower housing;
   d. force measuring means for measuring the amount of force being exerted when the top of the apparatus is pressed; and
   e. shift measuring means for measuring the distance said probe member moves beyond said base.

2. The apparatus as defined in claim 1 further comprising a controller means for receiving distance and force measurements simultaneously as one single measurement only when a predetermined force is attained, for directing an execution of one or more said single measurements of increasing increments of force for each succeeding said single measurement thereby constituting a measurement cycle, and for controlling the amount of force to be exerted at each succeeding increment of force.

3. The apparatus as defined in claim 2 further comprising a reset means for voiding all said single measurements from a preceding completed measurement cycle.

4. The apparatus as defined in claim 2 further comprising a signal means for conveying to a user that said apparatus is ready for use and for conveying to a user that one said measurement cycle has been completed.

5. The apparatus as defined in claim 2 wherein said controller means is programmable to establish the number of said single measurements constituting said measurement cycle, to control the amount of force to be executed at each succeeding increment of force, to establish the number of said measurement cycles to constitute a session, to automatically shutdown the force measuring means and the shift measuring means at the completion of each said measurement cycle, and to automatically reset said apparatus at the completion of each said measurement cycle.

6. The apparatus as defined in claim 5 further comprising an input means for conveying to said controller means the amount of force to be exerted at each said single measurement, for conveying to the controller means the number of said single measurements to be executed during each said measurement cycle, for conveying to said controller means the number of said measurement cycles to constitute each said single session, and for conveying to said controller means direction to retrieve any data derived from any said measurement cycle and any said session.

7. The apparatus as defined in claim 5 further comprising an output means for conveying to a user any one or more said single measurements, any one or more of said measurement cycles, and any data derived from any one or more said single measurements and any one or more said measurement cycles and any one or more said sessions.

8. The apparatus as defined in claim 5 further comprising a means for recording and storing each said measurement cycle completed for each said single session and means for deriving and storing an average for each said single session comprised of more than one said measurement cycle completed from that respective said single session.

9. The apparatus as defined in claim 8 further comprising a means for retrieving one or more said stored averages and for comparing said average of a current session to said average of any prior session.

10. The apparatus as defined in claim 1 wherein said means for slidably attaching said probe member to said lower housing comprises one or more slots vertically disposed on said probe member, said one or more said slots being normal to said plane, and said guide member traversing each of said one or more slots to thereby slidably retain said lower housing to said upper housing.

\* \* \* \* \*